US00PP10343P

United States Patent [19]

Grueber

[11] Patent Number: Plant 10,343

[45] Date of Patent: Apr. 21, 1998

[54] BRACHYCOME PLANT NAMED 'TOUCAN TANGO'

[75] Inventor: Garry Henry Grueber, Mainz, Germany

[73] Assignee: Innovaplant GmbH & Co. KG, Gensingen, Germany

[21] Appl. No.: 710,304

[22] Filed: Sep. 17, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Assistant Examiner*—Kent L. Bell

*Attorney, Agent, or Firm*—C. A. Whealy

[57] ABSTRACT

A distinct cultivar of Brachycome plant named 'Toucan Tango', characterized by its compact plant habit; dense and bushy plant form; fast crop time; freely branching plant habit; large inflorescences; numerous inflorescences with blue ray florets and bright yellow disc florets; and long, erect peduncles that hold inflorescences above the foliage.

2 Drawing Sheets

The present invention relates to a new and distinct cultivar of Brachycome plant, botanically known as a Brachycome hybrid and referred to by the cultivar name 'Toucan Tango'.

The new cultivar is a product of a planned breeding program conducted by the inventor in Gensingen, Germany. The objective of the breeding program was to develop compact cultivars with strong stems and large and numerous inflorescences.

The new cultivar originated from a cross made by the inventor in 1989 of an unidentified variety of *Brachycome rigidula*, as the male or pollen parent, with an unidentified variety of *Brachycome multifida*, as the female or seed parent. The cultivar Toucan Tango was discovered and selected by the inventor as a flowering plant within the progeny of the stated cross in a controlled environment in Gensingen, Germany.

Asexual reproduction of the new cultivar by terminal cuttings taken in Gensingen, Germany, has shown that the unique features of this new Brachycome are stable and are reproduced true to type in successive propagations.

The new cultivar has not been observed under all possible environmental conditions. The phenotype may vary somewhat with variations in environment such as temperature, daylength and light intensity, without, however, any variance in genotype.

Compared to plants of *Brachycome rigidula*, plants of the new Brachycome are denser and bushier and have more and larger inflorescences. Compared to plants of *Brachycome multifida*, plants of the new Brachycome are more compact, are denser and bushier, have stems that are more rigid and more and larger inflorescences.

The following characteristics have been repeatedly observed and are determined to be basic characteristics of 'Toucan Tango' which distinguish 'Toucan Tango' as a new and distinct cultivar:

1. Compact plant habit.
2. Dense and bushy plant form.
3. Fast crop time.
4. Freely branching plant habit.
5. Large inflorescences.
6. Numerous inflorescences with blue ray florets and bright yellow disc florets.
7. Long, erect peduncles that hold inflorescences above the foliage.

The accompanying colored photographs illustrate the overall appearance of the new cultivar, showing the colors as true as it is reasonably possible to obtain in colored reproductions of this type.

The first photograph comprises a side perspective view of a typical hanging basket plant of 'Toucan Tango'.

The second photograph comprises a close-up view of inflorescences of plants of 'Toucan Tango'.

Floret and foliage colors in the photographs may appear different from the actual colors due to light reflectance.

The following observations, measurements, values, and comparisons describe plants grown in Encinitas, Calif., under outdoor conditions. Color references are made to The Royal Horticultural Society Colour Chart except where general terms of ordinary dictionary significance are used.

Classification:

*Botanical.*—Brachycome hybrid cultivar 'Toucan Tango.'

*Commercial.*—Brachycome.

Parentage:

*Male or pollen parent.*—*Brachycome rigidula.*

*Female or seed parent.*—*Brachycome multifida.*

Propagation:

*Type.*—By cuttings.

*Time to initiate and develop roots.*—Summer: About 20 days at temperatures of 22° C. Winter: About 25 days at temperatures of 20° C.

*Rooting habit.*—Fibrous and freely branching.

Plant description:

*General appearance.*—Rounded, spreading, dense and bushy herbaceous plant with lacy pinnatifid foliage and erect flower stems that hold the inflorescences about 3 cm above the foliage. Appropriate for 12.5 pots to 25-cm hanging basket containers.

*Plant height.*—About 15 cm from soil level to top of inflorescences.

*Branching.*—Freely branching.

*Growth rate.*—Moderate.

*Vigor.*—Moderate.

*Stem color.*—144A.

*Foliage description.*—Arrangement: Alternate, single. Leaf shape: Pinnatifid. Leaf apex: Acute. Leaf Base: Attenuate. Leaf margin: Deeply lobed, about 3 lobes per side. Leaf aspect: Flat. Leaf length: About 3.5 cm. Leaf width: About 2.7 cm. Leaf texture: Leathery, glabrous. Leaf color: Young leaves: Abaxial surface: 144A. Adaxial surface: 144A. Fully expanded leaves: Adaxial surface: 147A. Abaxial surface: 137A. Venation: Very faint, inconspicuous.

Flowering description:

*Inflorescence.*—Single daisy-type composite inflorescence form. Florets arranged acropetally on a capitulum. Inflorescences last on the plant for 3 to 4 weeks. Inflorescences persistent.

*Natural flowering season.*—Natural flowering season in spring to early fall. Plants flower recurrently during this period.

*Inflorescence diameter.*—2.5 to 3 cm.

*Inflorescence depth (height).*—About 5 mm.

*Fragrance.*—None.

*Ray florets.*—Shape: Elliptic. Apex; Obtuse. Base: Attenuate. Margin: Entire. Length: 1 to 1.25 cm. Width: 2 to 3 mm. Texture: Smooth, glabrous. Color: When opening: Adaxial surface: 90B. Abaxial surface: 91C. Mature: Adaxial surface: 90B. Abaxial surface: 91C. After anthesis: Adaxial surface: 90B. Abaxial surface: 91D. Number of ray florets per inflorescence: About 30.

*Disc florets.*—Shape: Tubular. Diameter of disc: 0.5 to 1 cm. Disc floret length: About 3 mm. Disc floret width: About 1 mm. Color: Immature: 144A. Mature: 6A. Number of disc florets per inflorescence: About 32.

*Peduncle.*—Length: First peduncle: About 3 cm. Fourth peduncle: About 6 cm. Strength: Moderately strong, inflorescences held erect above foliage. Texture: Smooth, rounded. Color: 144A.

*Flower bud.*—Shape: Spherical and slightly flattened. Length: About 3 mm. Diameter: About 4 mm.

*Androecium.*—Anther color: 6A. Pollen color: 6A. Amount of pollen: Moderate

*Gynoecium.*—Pistil number: One per floret. Stigma shape: Bilobate. Style lenth: About 3 mm.

Disease resistance: No susceptibility nor resistance to fungal, bacterial or viral pathogens has been noted.

Seed production: Seed production is typically not observed.

It is claimed:

1. A new and distinct Brachycome plant named 'Toucan Tango', as illustrated and described.

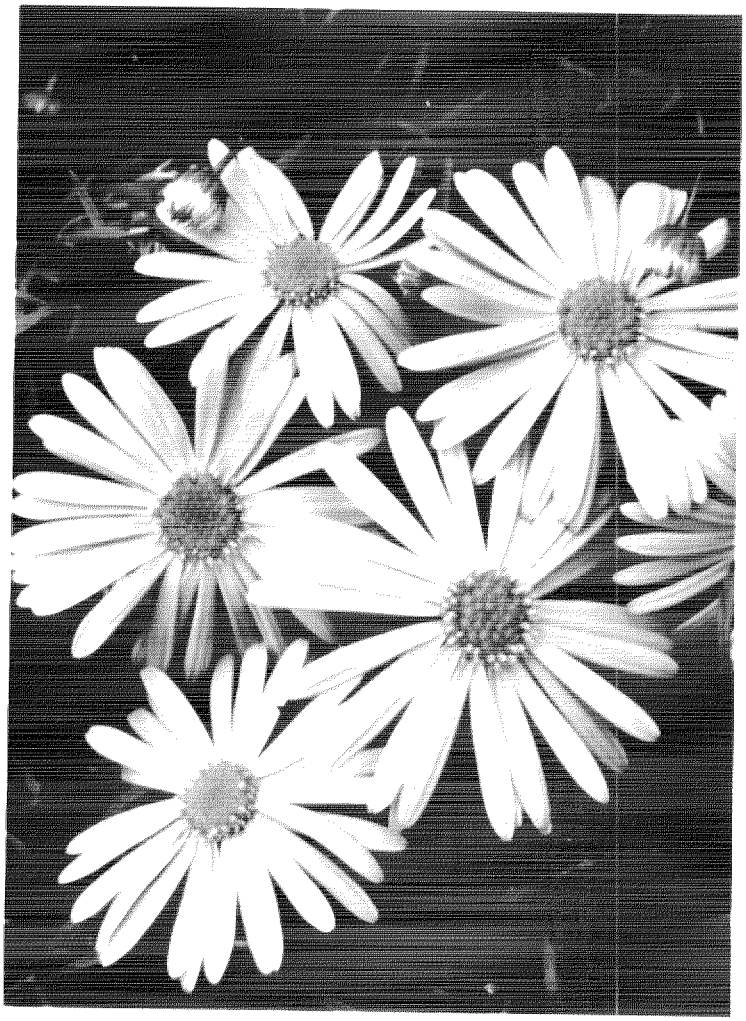

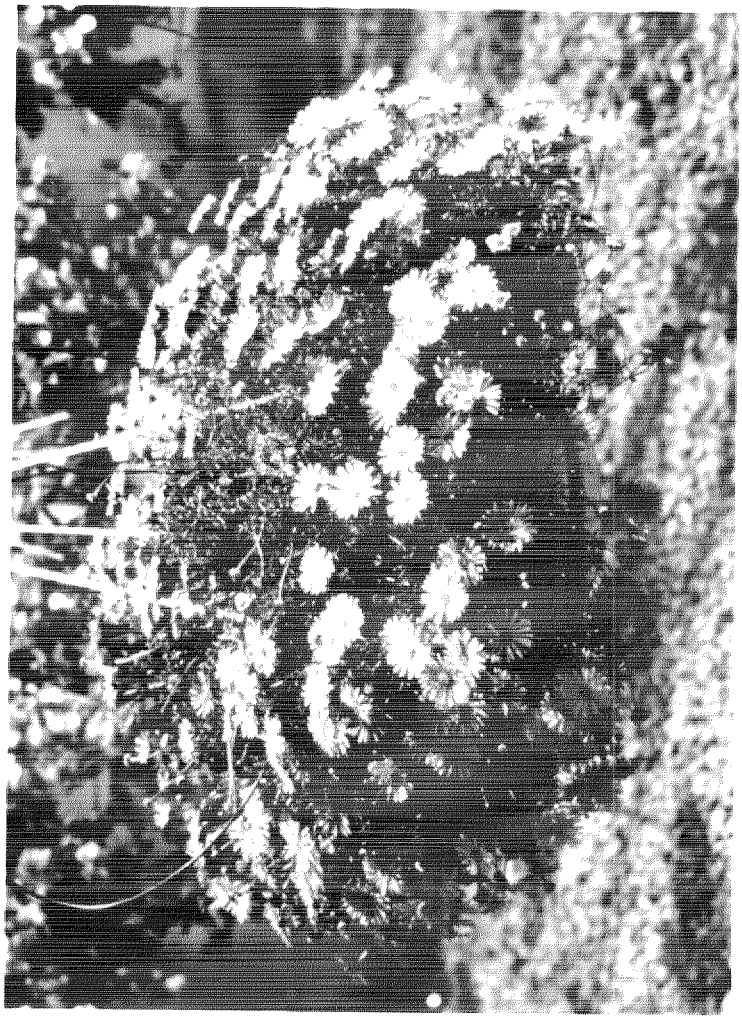

* * * * *